United States Patent
Putz

(10) Patent No.: US 7,608,064 B2
(45) Date of Patent: Oct. 27, 2009

(54) DEPTH PROBE FOR INTRACRANIAL TREATMENT

(75) Inventor: David Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 11/736,828

(22) Filed: Apr. 18, 2007

(65) Prior Publication Data
US 2007/0191791 A1    Aug. 16, 2007

Related U.S. Application Data

(63) Continuation of application No. 11/262,377, filed on Oct. 28, 2005, now abandoned, which is a continuation-in-part of application No. 10/423,587, filed on Apr. 25, 2003, now Pat. No. 7,241,283.

(51) Int. Cl.
    *A61M 5/00*    (2006.01)
(52) U.S. Cl. .......... 604/264; 604/20; 604/158; 604/103.01; 607/3; 607/115
(58) Field of Classification Search .......... 604/20–21, 604/65–67, 103.01–103.02, 158, 264; 600/585, 600/561; 607/2, 3, 115–116; 606/47–48
See application file for complete search history.

(56) References Cited

U.S. PATENT DOCUMENTS

| | | | | |
|---|---|---|---|---|
| 5,832,932 A | * | 11/1998 | Elsberry et al. | 128/898 |
| 6,510,347 B2 | * | 1/2003 | Borkan | 607/117 |
| 6,558,353 B2 | * | 5/2003 | Zohmann | 604/158 |

\* cited by examiner

*Primary Examiner*—Nicholas D Lucchesi
*Assistant Examiner*—Theodore J Stigell
(74) *Attorney, Agent, or Firm*—Jansson Shupe & Munger Ltd.

(57) ABSTRACT

A depth probe for intracranial treatment is provided having a body that includes a distal portion with one aperture and at least one element mounted upon the exterior surface, a lumen defined by the body that is accessed only through the aperture and an opening, and a proximal portion with at least one proximal-contact radially circumscribing the body. The proximal-contact is conductively connected with the element. The lumen is sized to receive coaxially an inner catheter adapted to transfer a fluid such as a drug with a tissue region within the patient's brain. The aperture is coaxial with the lumen and sized to allow the inner catheter to pass through it. The depth probe preferably includes an inflatable balloon secured upon its distal portion proximal to the element. The balloon is adapted to seal upon inflation the tract created by the probe when inserted into the brain.

21 Claims, 5 Drawing Sheets

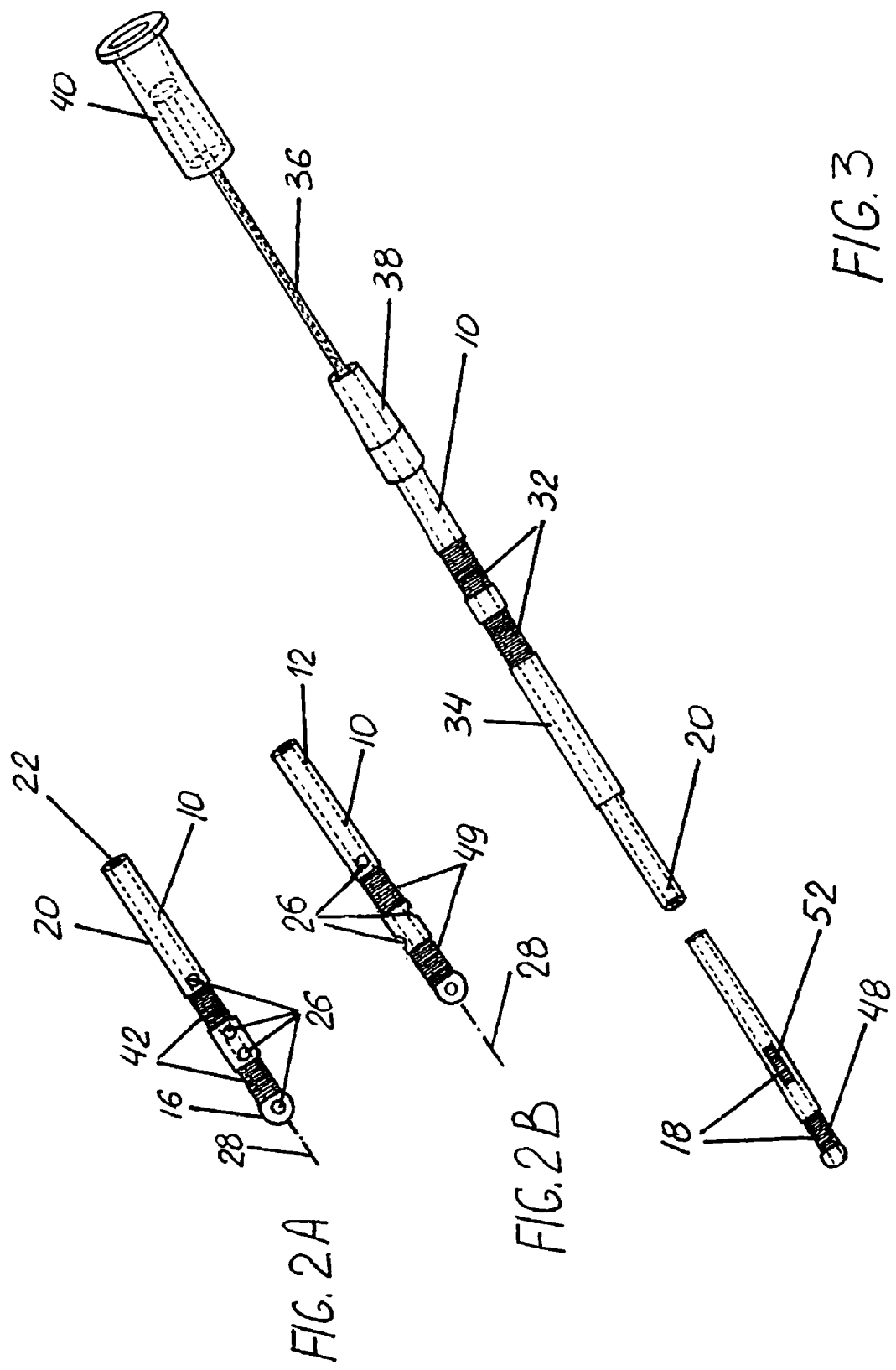

DEPTH PROBE FOR INTRACRANIAL TREATMENT

RELATED APPLICATION

This application is a continuation of U.S. patent application Ser. No. 11/262,377, filed on Oct. 28, 2005, now abandoned, which is a continuation-in-part of U.S. patent application Ser. No. 10/423,587, filed on Apr. 25, 2003, now U.S. Pat. No. 7,241,283.

FIELD OF INVENTION

The present invention relates to instrumentation utilized for intracranial treatment and, in particular, to depth probes utilized for intracranial treatment.

BACKGROUND OF THE INVENTION

Movement disorders such as epilepsy and Parkinson's disease have been estimated to affect some 1-2% of the developed world's population and up to 10% of people in underdeveloped countries. Currently, approximately 75% of those who suffer from movement disorders are responsive in some degree to drugs.

Electrical stimulation has also been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

In treatment, electrical stimulation has been used with the recording and analysis of changes in brain activity to predict the occurrence of epileptic seizures. The time of onset of such seizures is often predictable by neural discharge monitoring, even when the exact causal nature of precipitating dysfunction is not understood. Electrodes have been used to obtain signals representative of current brain activity along with a signal processor for continuous monitoring and analysis of these electrical signals in order to identify important changes or the appearance of precursors predictive of an impending change.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

Improved intracranial monitoring devices have been shown to facilitate treatments of movement disorders. Monitoring is typically performed by instruments which are inserted into the brain at different locations or along different tracks. Other systems employ a single device which must be removed and reinserted to provide for delivery of multiple drugs or use of different electrical devices.

Since the introduction of probes or other similar devices into the brain is common in many surgical procedures today, there are a variety of probes available. Such probes typically include ports for drug delivery or electrical, chemical, electrochemical, temperature and/or pressure contacts which enable the observation and analysis of the brain state or contacts providing stimulation. These ports and contacts must typically be positioned at specific points or regions in the brain.

Probes used in intracranial penetration are typically fabricated so that their introduction to the brain is as minimally traumatic as possible. In addition to being minimally traumatic during insertion, certain inserted probes must also be able to remain implanted without causing injury through unintended movement. In some uses, a probe may be implanted and remain in the patient's brain for weeks or longer. Changes in the positioning of the probe often occur during placement or during such extended periods. Therefore, the probe must be capable of precise placement and as bio-compatible as possible. In response to these requirements, state of the art intracranial probes are typically thin, flexible pieces with smooth surfaces to minimize the amount of brain tissue contacted and to minimize damage to contacted brain tissue.

While such thin, flexible probes are sufficiently bio-compatible, they are delicate and often difficult to insert along specific trajectories or lines of insertion. During typical implantation, a surgeon feeds the probe into the brain through an aperture in the skull. In this process, the surgeon has very little control over the distal end of the probe. In order to provide more rigidity to the probe to overcome this problem, a removable stylet may be inserted into the probe before implantation. Still, veering from the intended line of insertion is not altogether prevented by introduction of a stylet to the probe.

There is a continuing significant need in the field of intracranial treatment, particularly with insertion of probes into the interior of the brain, for improvements in accuracy of insertion and avoidance of injury, while retaining efficiency and ease of use.

In addition, there is a need in the field of intracranial treatment to minimize the invasiveness of intracranial treatment and to reduce the number of instruments which penetrate brain tissue or the number of times a single instrument must penetrate brain tissue.

Furthermore, there is a need in the field of intracranial treatment to provide the ability to precisely locate the position of a probe during insertion to ensure proper positioning.

OBJECTS OF THE INVENTION

It is a primary object of the invention to provide an improved depth probe for intracranial treatment of a patient that overcomes some of the problems and shortcomings of the prior art.

Another object of the invention is to provide a novel depth probe that is simple in structure and operation in order to facilitate intracranial procedures.

Another object of the invention is to provide an exceptional depth probe having a body adapted to avoid extensive trauma to and scarring of brain tissue.

Another object of the invention is to provide an excellent depth probe having a body that includes contacts for stimulation and/or for monitoring of the brain.

Another object of the invention is to provide a desirable depth probe having a lumen for receiving and guiding an inner catheter for the delivery of a drug to targeted brain tissue and that can remain in position when the inner catheter is removed, thereby permitting repeated insertions of different inner catheters without extended contact with brain tissue during insertion.

Another object of the invention is to provide an exceptional depth probe that provides an attached connector conductively connected to a plurality of monitoring and sensing elements for efficient and effective transmission of readings from the elements to external analysis and control devices.

Yet another object of the invention is to provide a novel depth probe having a distal portion provided with an inflatable balloon capable of sealing off the insertion tract formed by the probe to prevent a drug being introduced into the brain by the probe from migrating back through the tract and further allows for the monitoring of cellular function within the brain prior to and after introduction of the drug.

SUMMARY OF THE INVENTION

The invention is for a depth probe utilized to provide intracranial treatment of a patient. The depth probe comprises a body with an exterior surface and an opening, a distal portion of the body having one aperture and at least one element mounted upon the exterior surface, a lumen defined by the body that is accessed only through the aperture and the opening, and a proximal portion of the body with at least one proximal-contact radially circumscribing the body. The proximal-contact is conductively connected with the element. The term "conductively connected" is meant to include a connection via a lead in the form of a wire or fiber-optic bundle for the transmission of electrical and/or optical signals.

The lumen has an axis and is sized to receive coaxially an inner catheter adapted to transfer a fluid such as a drug with a tissue region within the patient's brain. The aperture is coaxial with the lumen and is sized to allow the inner catheter to pass through it.

A number of highly preferred embodiments have the body made from substantially inflexible material.

One preferred embodiment finds the opening on the body having a tapered fitting so that a pumping instrument can be connected to the probe at the fitting for the transfer of a fluid with a tissue region of the patient's brain. Much preferred is where the opening is at the proximal end of the body and coaxial with the lumen.

In certain preferred cases, the element is a contact that can provide electrical stimulation to tissue regions within the patient's brain. Also desirable is where the element is a contact that monitors activity, preferably electrical activity, within the patient's brain. More desirable is where the probe has a plurality of contacts spaced axially along its distal portion, each of these contacts being a macro-contact that collars, i.e., circumscribes, the body. Highly desirable is where the contact is a micro-contact and preferably where the probe has a plurality of micro-contacts spaced axially and radially along its distal portion.

Another appreciated embodiment finds the element to be a sensor. Much preferred is where the sensor senses chemical activity within the brain. Another element found desirable is where it is a location marker that allows the position of the distal portion of the probe to be identified when it is inserted into the brain. This embodiment is especially desirable when the marker is adapted to be identified, i.e. seen, under magnetic resonance imaging.

One very preferred example of this invention is where there are a plurality of proximal-contacts spaced axially along the proximal portion. Most preferred is where a connector adapted to receive these proximal-contacts is secured to the body. It is desirable that each of these proximal-contacts be in electrical communication with a micro-contact. More desirable is where the connector extends outward from the body and has a housing formed to position the proximal-contacts in a linear array. The connector in this embodiment has a lead-conduit extending from this housing that connects it to the body of the probe. A highly preferred embodiment finds the connector as being firmly attached to the body.

Another highly desirable embodiment is where the proximal portion of the body has a first diameter and its distal portion has a second diameter such that the second diameter is less than the first diameter. Having this structure, the degree of contact with the tissue region by the body is reduced when the probe is inserted into the brain.

Another interesting embodiment of this invention finds the depth probe including a conduit extending from its proximal portion to an inflatable balloon secured upon its distal portion. Much desired is where the balloon is inflatable with at least one drug and the balloon is formed from a material permeable to this drug so that the drug can be introduced into the tissue region through the balloon. Also preferred is where the balloon is adapted to seal upon inflation the tract created by the probe upon its insertion into the brain.

A most desirable embodiment has the balloon positioned along the distal portion of the body at a point proximal to the aperture. Highly preferred is where the balloon is positioned along the distal portion and is also proximal to the element on the probe.

BRIEF DESCRIPTION OF THE DRAWINGS

FIGS. 2A and 2B are perspective views of the distal portions of alternate preferred depth probes in accordance with this invention with dashed lines to represent otherwise unseen internal features.

FIG. 3 is a perspective view of another preferred depth probe in accordance with this invention receiving an inner catheter with cut-away sections to reveal and dashed lines to represent otherwise unseen internal features.

DETAILED DESCRIPTION OF PREFERRED EMBODIMENTS

Figure 1:
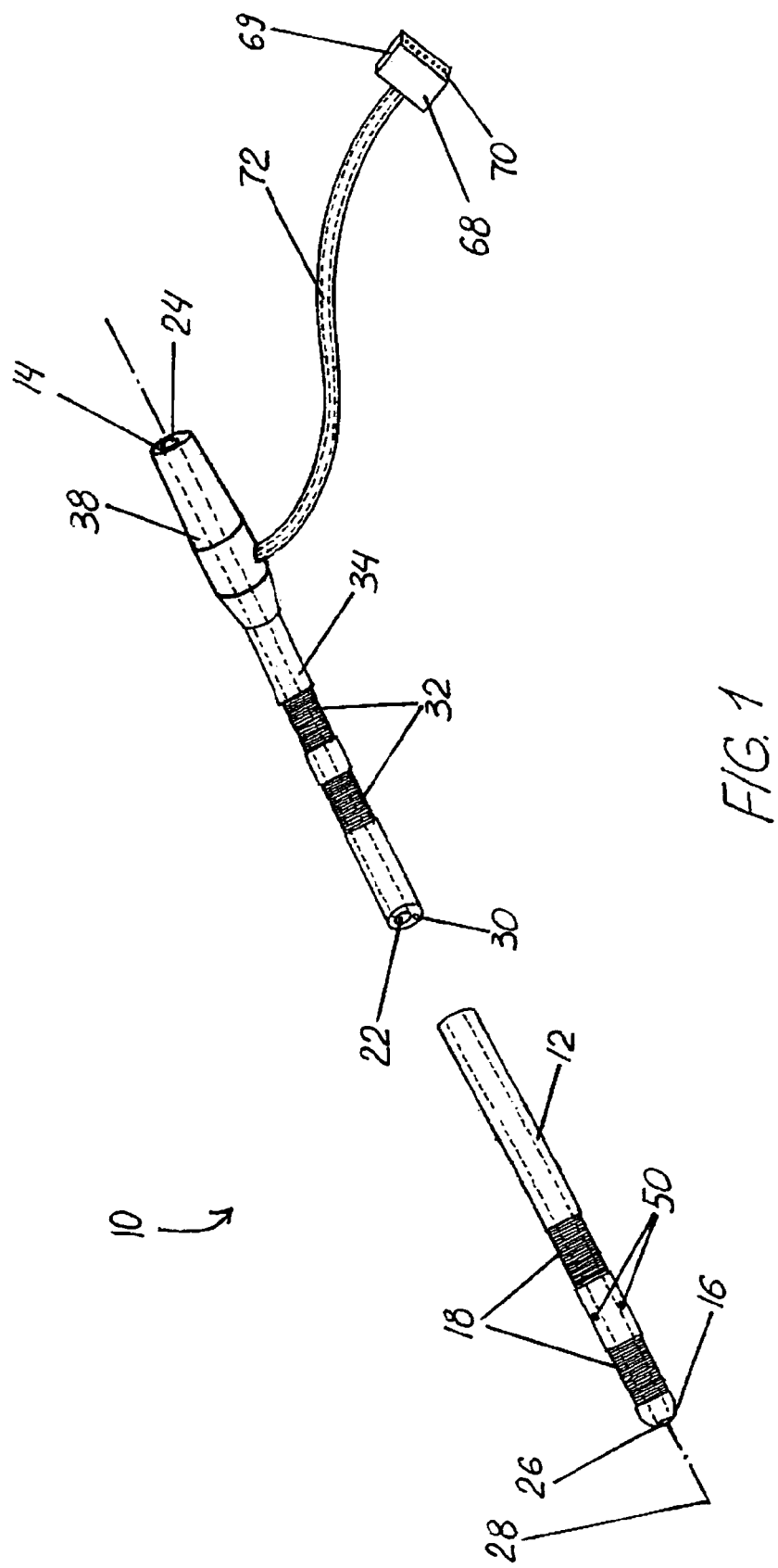
FIG. 1 is a perspective view of a preferred depth probe having a connector extending outward from the body in accordance with this invention with cut-away sections to reveal and dashed lines to represent otherwise unseen internal features.

The figures illustrate preferred embodiments of an improved depth probe for intracranial treatment of a patient in accordance with this invention. FIG. 1 is a perspective view of depth probe 10 having an elongated, tubular body 12 extending from proximal end 14 to distal end 16. Body 12 preferably has a diameter between about 0.6 and 3.0 millimeters, most preferably about 1.0 millimeter.

As seen in FIG. 1, body 12 includes elements 18 secured to distal portion 20 at distal end 16. Body 12 is also provided with lumen 22 extending from opening 24 at proximal end 14 and in communication with aperture 26. Lumen 22 is a tubular channel extending for some length within body 12, preferably having a diameter of 0.5 millimeters or less. Body 12 is open at distal end 16 to form aperture 26. Opening 24 and aperture 26 are coaxial with lumen 22 along central axis 28 of body 12.

Elements 18 are conductively connected by leads 30 (seen in FIG. 1 running alongside lumen 22) to proximal-contacts 32. Leads 30 can be in the form of electrical wiring or a fiber-optic bundle. Proximal-contacts 32 are mounted along proximal portion 34 of body 12. When depth probe 10 is inserted into the brain, proximal-contacts 32 remain outside of the patient. Proximal-contacts 32 are preferably formed from stainless steel or similar alloys or materials that are non-corrosive conductors and that can endure sterilization.

Depth probe 10 can be substantially flexible, formed from bio-compatible materials such as polyurethane, silicone, or polyimide. Body 12 can also be in the form of a cannula where body 12 is made from a substantially rigid material that is preferably MRI safe/compatible. Such preferable materials are platinum, titanium, polyimide-coated glass, and other non-ferrous alloys. During surgery, when in the form of a cannula, depth probe 10 may be used with a stereotatic frame or a frameless guidance system to accurately position the catheter within the brain.

As seen in FIGS. 2A and 2B, preferred embodiments of depth probe 10 can have a closed distal end 16 and a plurality of apertures 26, each aperture 26 in communication with lumen 22. Apertures 26 in FIG. 2A are positioned above distal end 16 and spaced in axial alignment with axis 28 along distal portion 20. Apertures 26 in FIG. 2B are shown axially and radially spaced about axis 28. One skilled in the art will recognize that these configurations can also include an aperture 26 forming an open distal end 16 as depicted in FIG. 1.

Body 12 of depth probe 10 may also include a distal portion 20 having a reduced diameter as illustrated in FIG. 3. Such a configuration for distal portion 20 allows for reduced injury to the surrounding tissue regions during the insertion of depth probe 10 into the brain.

As depicted in FIG. 3, lumen 22 is preferably sized so as to be able to receive an inner catheter 36, i.e., lumen 22 is provided with a diameter slightly greater than the outside diameter of inner catheter 36. After positioning the distal end 16 of depth probe 10 in a targeted region of the brain, inner catheter 36 can be inserted into opening 24 and guided by lumen 22 to this tissue area. Inner catheter 36 can be withdrawn and reinserted or different inner catheters 36 can be inserted into depth probe 10 without reinserting or repositioning depth probe 10. Inner catheter 36 is preferably polyimide, polyimide-coated glass or other similar material. Applicant notes that one such preferred catheter is disclosed in U.S. patent application Ser. No. 10/423,587 filed by Applicant on Apr. 25, 2003, the disclosure of which is incorporated by reference herein.

Proximal end 14 of body 12 is provided with a tapered fitting 38, preferably a male luer conical fitting, to provide for a detachable fluid-tight coupling with some external device. The proximal end of inner catheter 36 is provided with a tapered coupler 40, preferably a luer coupler that has female luer fittings at both of its ends. Tapered coupler 40 enables inner catheter 36 to form a liquid-tight joint with depth probe 10 when inner catheter 36 is fully inserted into lumen 22 through opening 24. Coupler 40 enables inner catheter 36 to be operatively connected by tubing to an external piece of equipment such as a pump. One skilled in the art will recognize that inner catheter 36 could also be connected to internal instrumentation having pumping capability. This process enables fluids such as drugs to be administered to the brain through inner catheter 36.

Elements 18 provide for monitoring of brain activity, for stimulating brain tissue or for serving as a location beacon to aid in determining the precise position of distal portion 20 within the brain. Elements 18 can take the form of contacts 42, as illustrated in FIGS. 1-6. Contacts 42 comprise devices such as electrodes 44 designed to monitor brain activity in a selected tissue region of the brain 46 through the sensing of electrical and/or electrochemical changes within the brain as well as electrodes 48 designed to provide electrical stimulation to specific areas of the brain. Electrodes serving as contacts 42 are preferably constructed from platinum, platinum-iridium or other bio-compatible conductive material. Electrodes can be macro-contacts 49 that circumscribe or band body 12 or micro-contacts 50 capable of measuring electrical changes at the level of a single neuron.

Elements 18 can also can take the form of a sensor 52 as depicted in FIG. 3. Sensors 52 are designed to monitor brain activity within select tissue regions through the sensing of electrical, electrochemical, chemical, temperature or pressure changes within the brain. Sensors 52 can be electrochemical and optical transducers designed to measure chemical, pressure, temperature, cerebral blood flow and other physiological changes in the brain. Such devices are known in the art and are preferably less than about 2 millimeters long. Sensor 52 is preferably in the form of a chemical sensor.

Elements 18 may further be in the form of a location marker 54 as seen in FIGS. 5A and 5B. Location marker 54 is preferably a structure comprised of a non-ferrous material known in the art such as gold or tungsten that has an image signal intensity suitable for proton magnetic resonance imaging (MRI) with most commercial machines and is also sufficiently x-ray opaque for satisfactory imaging using computed tomographic scanning (CT) or on X-ray. Location marker 54 can also be comprised of a sensor capable of measuring voltages induced by a transmitted magnetic field that can be used to identify the position and orientation of the sensor within that field.

Elements 18 may be positioned on both the distal and proximal sides of apertures 26 along distal portion 20 as seen in FIGS. 2A and 2B. This configuration allows for monitoring of cellular function within the tissue region of the brain 46 being targeted prior to treatment to verify the presence of diseased brain cells. Upon verification of diseased tissue within the targeted region, delivery of a drug or other treatment agent can commence through depth probe 10 while monitoring of the tissue region 46 continues concurrently with such treatment. This can have particular value in the treatment of different tissue regions of the brain for movement disorders such as Parkinson's Disease.

Figure 4:
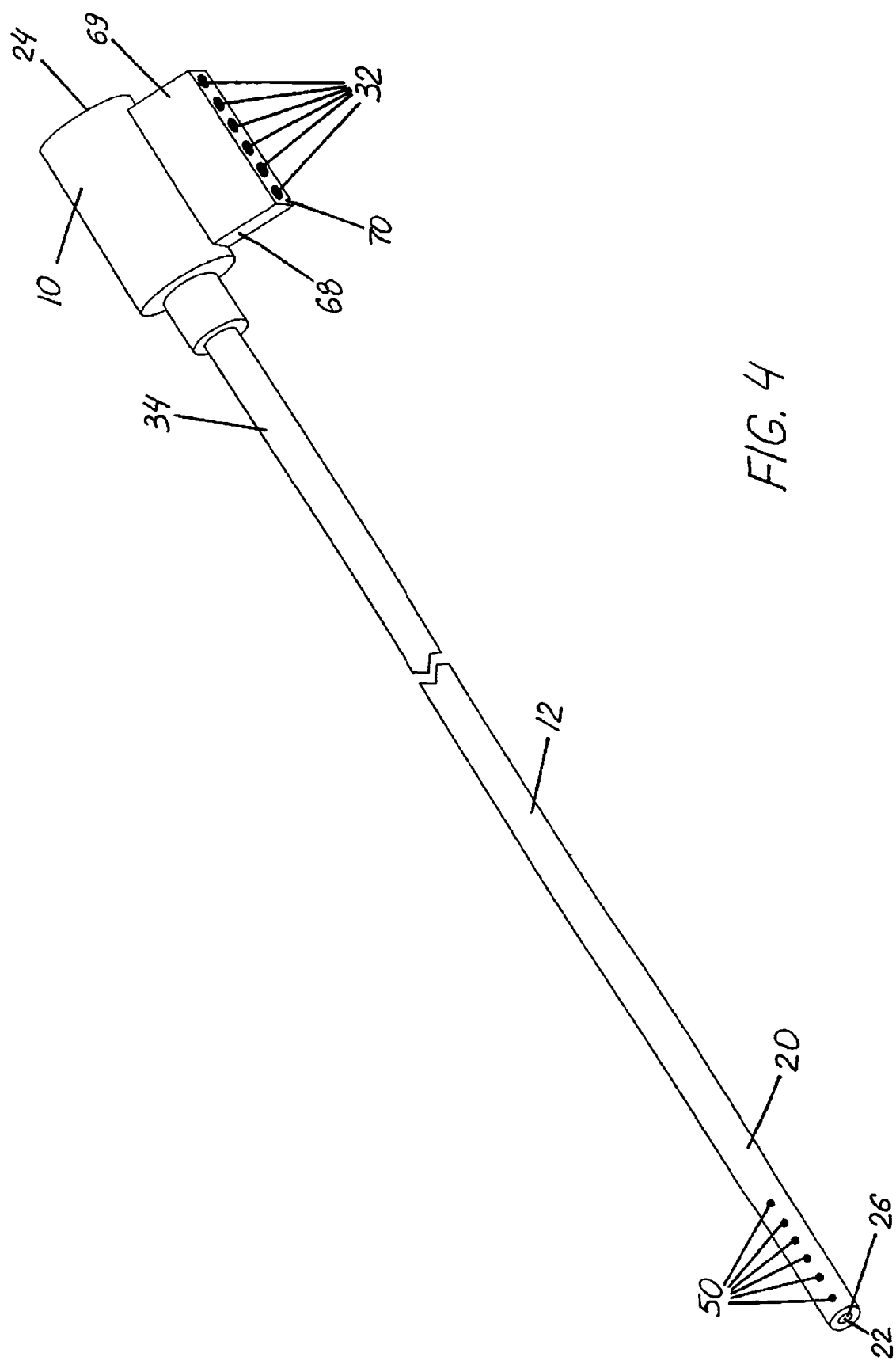
FIG. 4 is a perspective view of an alternate embodiment of the depth probe having a connector attached to the body in accordance with this invention with a cut-away section.
Figure 5:
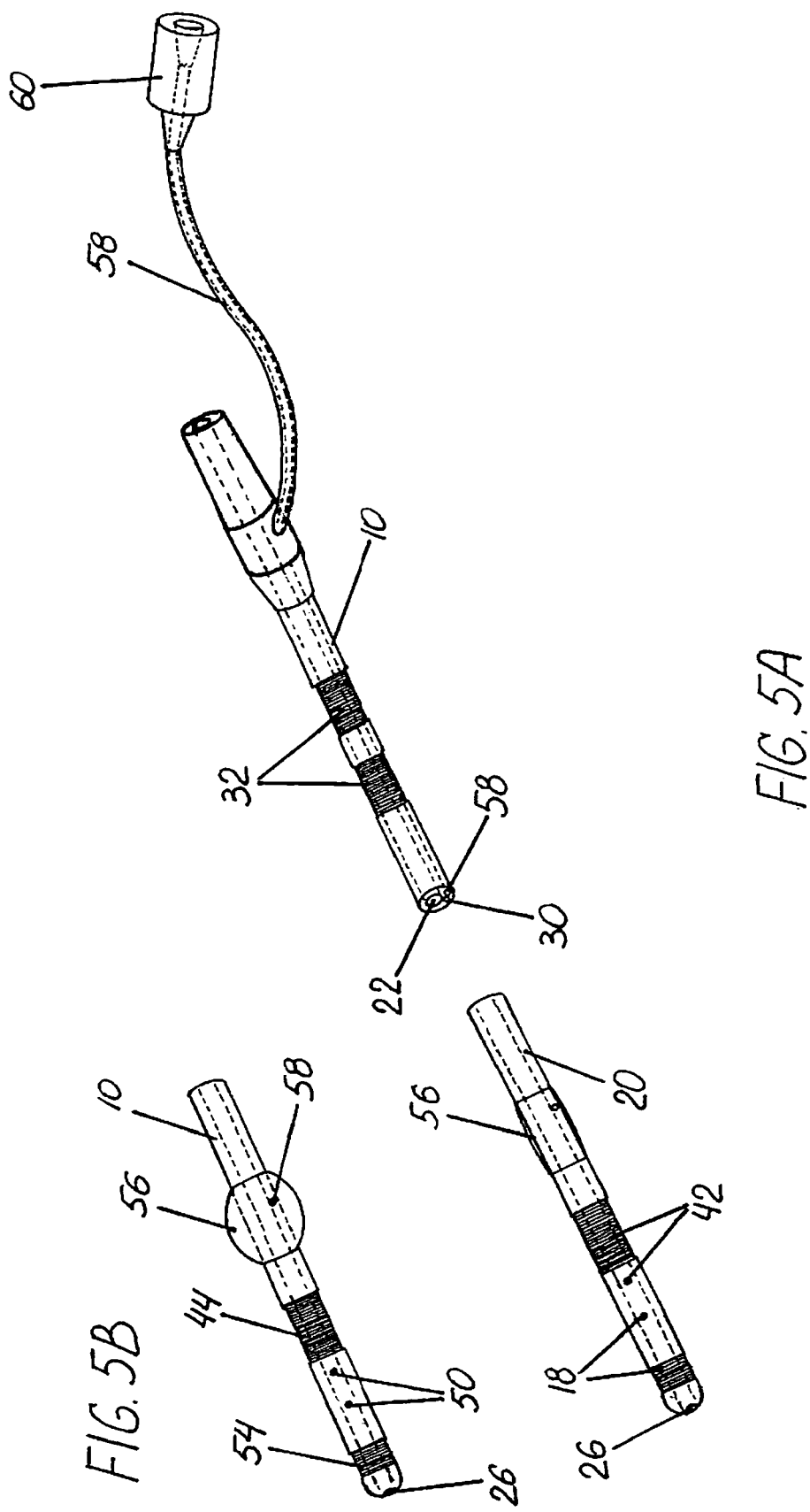
FIG. 5A is a perspective view of a preferred depth probe having a balloon shown deflated in accordance with this invention with cut-away sections to reveal and dashed lines to represent otherwise unseen internal features.
FIG. 5B is the distal end of the depth probe of FIG. 5A showing the balloon inflated with cut-away sections to reveal and dashed lines to represent otherwise unseen internal features.

FIGS. 1, 2, 5A and 5B show that macro-contacts 49 are spaced axially along distal portion 20. Micro-contacts 50 can be spaced axially along distal portion 20 as illustrated in FIG. 4 or spaced radially around body 12 as shown in FIG. 1.

FIGS. 5A and 5B illustrate a depth probe 10 having an inflatable balloon 56 rigidly mounted to distal portion 20, preferably above at least one element 18 and at least one aperture 26. As seen in FIG. 5A, a conduit 58 enters body 12 along proximal portion 34 and runs alongside lumen 22, terminating at balloon 56. Conduit 58 is preferably tubing made of polyurethane. Conduit 58 provides for the introduction of a fluid to inflate balloon 56 and, if necessary to withdraw fluid from balloon 56 to cause deflation. Conduit 58 originates at injection port 60 that can be operatively connected to an external device 62 such as a pump to dispense or receive fluid.

Figure 6:
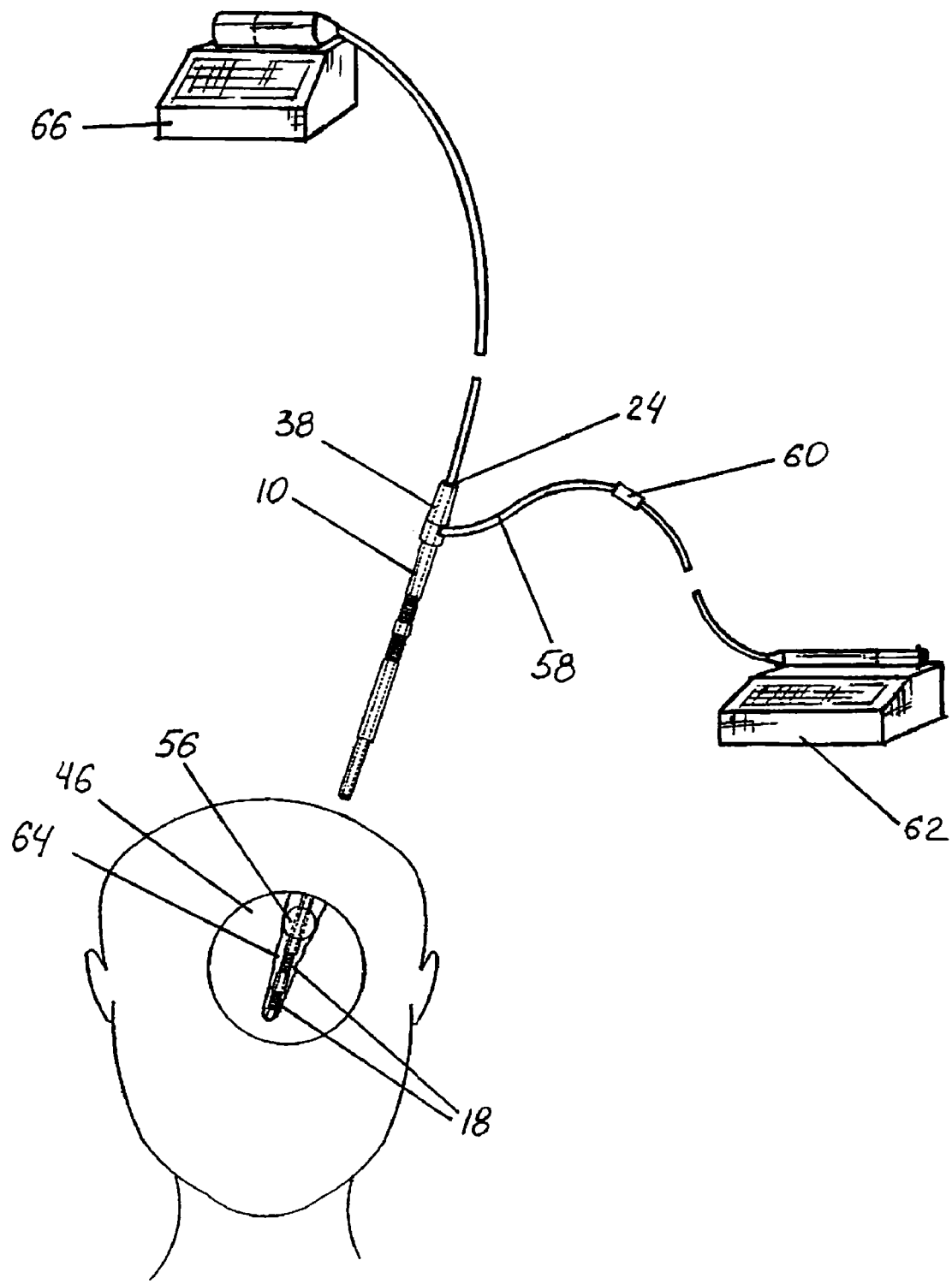
FIG. 6 is a schematic view illustrating the depth probe of FIGS. 5A and 5B positioned within the brain.

As depicted in FIG. 6, following placement of distal portion 20 of depth probe 10 within the brain, balloon 56 can be inflated to block or occlude the insertion tract 64 created during the insertion process so that any drug administered to the brain 46 through aperture 26 cannot migrate back through that tract. Balloon 56 is preferably made from an elastomeric material to achieve complete deflation of balloon 56 when depth probe 10 is later withdrawn from the brain.

In certain embodiments, balloon 56 is permeable. Balloon 56 in these embodiments can be inflated with a drug or other fluid intended to be administered to the brain whereby the drug then permeates through the wall of balloon 56 to treat the tissue region of the brain 46 surrounding balloon 56. In this manner, a drug can be introduced to one targeted tissue region of the brain delivered by depth probe 10 through aperture 26 at the same time the same or a different drug is transferred to another selected tissue region through permeable balloon 56. Balloon 56 is preferably adapted to administering a drug to the brain slowly over a period of time, thereby allowing for the effective introduction of the drug to the desired tissue region. This is especially desirable where there is a void in the particular tissue region due to some structure such as a tumor being removed. Inflating balloon 56 within the void permits the medication to be more effectively transferred to all of the affected tissue that surrounds the outside of the balloon.

One skilled in the art will recognize that balloon 56 can be made permeable by forming balloon 56 from a naturally porous material such as polytetrafluroethylene (PTFE) or from an elastomeric material having perforations formed in the wall of the balloon. The balloon wall is preferably from 0.5 to 5.0 mils in thickness. Where the balloon wall is perforated, an array of minute perforations, each having a diameter of 5 to 30 microns, is preferably uniformly spaced apart and concentrated along a central band circumscribing balloon 56. Concentration of the perforations within such a region in the middle of balloon 56 provides for focused delivery of the drug by limiting the area of permeation to just the surface area of balloon 56 making conforming contact with the surrounding brain tissue.

Tapered fitting 38 enables depth probe 10, as shown in FIG. 6, to form a liquid-tight seal with tubing or similar conduit having a female luer connector. In this manner, opening 24 of body 12 is operatively connected by the tubing to an external instrument such as pumping equipment 66. One skilled in the art will recognize that depth probe 10 could also be connected to internal instrumentation having pumping capability. Such equipment allows fluids to be transferred to or from tissue region of the brain 46 through any aperture 26. Drugs can then be administered to the brain, cerebral spinal fluid can be withdrawn, or both.

Depth probe 10, as illustrated in FIGS. 1 and 4, can also include a connector 68. Connector 68 comprises a housing 69 mounting a linear array 70 of proximal-contacts. Connector 68 is conductively connected via additional leads 30 to elements 18, preferably micro-contacts 50, along distal portion 20. Connector 68 can be rigidly mounted to body 12 along its proximal portion 34 as shown in FIG. 4.

Connector 68 can also extend outward from body 12 as seen in FIG. 1. Connector 68 in this embodiment is secured to body 12 by lead-conduit 72. Leads 30 that originate at connector 68 pass through lead-conduit 72 before entering body 12 at a point along proximate portion 34 to proceed along lumen 22 to the corresponding elements 18.

One skilled in the art will readily recognize that proximal-contacts 32 are in an axial alignment that adapts them to being conductively connected to an external connector (not shown) in operative communication with a computer or similar instrument having a conventional output display and monitor with a suitable power source. This enables the brain activity sensed by elements 18 linked to these proximal-contacts to be recorded and/or analyzed and/or control over elements 18 to be exercised.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A depth probe for intracranial treatment of a patient comprising:
   a body extending from a proximal end to a distal end and having an exterior surface and an opening;
   a distal portion of the body at the distal end having one aperture and at least one element mounted upon the exterior surface;
   a lumen defined by the body with access thereto being limited to only the opening and the aperture, the lumen having an axis and being sized to receive coaxially an inner catheter for transferring a fluid with a tissue region within the patient's brain and the aperture being coaxial with the lumen and being sized to allow the inner catheter to pass therethrough; and
   a proximal portion of the body at the proximal end having at least one proximal-contact radially circumscribing the body, the proximal-contact being conductively connected with the at least one element, and a tapered fitting at the proximal end, the tapered fitting being sized to be received by a tapered coupler of the inner catheter to form a liquid-tight connection with the inner catheter when the inner catheter is fully inserted into the lumen.

2. The depth probe of claim 1 wherein the body is made from substantially rigid material.

3. The depth probe of claim 1 wherein the tapered fitting is further adapted to connect to a pumping instrument for transferring a fluid with a tissue region within the patient's brain.

4. The depth probe of claim 3 wherein the opening is at the proximal end and coaxial with the lumen.

5. The depth probe of claim 1 wherein the element is a contact that provides electrical stimulation to a tissue region within the patient's brain.

6. The depth probe of claim 1 wherein the element is at least one contact that monitors activity within the patient's brain.

7. The depth probe of claim 6 wherein the contact monitors electrical activity within the patient's brain.

8. The depth probe of claim 6 wherein the at least one contact is a plurality of contacts radially circumscribing the body and spaced axially along the distal portion.

9. The depth probe of claim 6 wherein the contact is a micro-contact.

10. The depth probe of claim 9 wherein the at least one contact is a plurality of micro-contacts spaced axially or radially along the distal portion.

11. The depth probe of claim 1 wherein the element is at least one sensor.

12. The depth probe of claim 11 wherein the sensor senses chemical activity within the patient's brain.

13. The dept probe of claim 1 wherein the element is a location marker to identify the position of the distal portion when the probe is inserted into the brain.

14. The depth probe of claim 13 wherein the location marker is adapted to be identified by magnetic resonance imaging.

15. The depth probe of claim 1 wherein the proximal-contact is in electrical communication with a micro-contact.

16. The depth probe of claim 1 wherein the proximal portion has a first diameter and the distal portion has a second diameter such that the second diameter is less than the first diameter to reduce the degree of contact with the tissue region by the body when the probe is inserted into the brain.

17. The depth probe of claim 1 wherein the at least one proximal-contact is a plurality of proximal-contacts spaced axially along the proximal portion.

18. The depth probe of claim 1 further comprising a conduit extending from the proximal portion to an inflatable balloon secured to the distal portion.

19. The depth probe of claim 18 wherein the balloon is inflatable with at least one drug and the balloon is formed from a material permeable to the drug such that the drug can be introduced into the tissue region through the balloon.

20. The depth probe of claim 18 wherein the balloon is adapted to seal upon inflation a tract created upon insertion of the probe into the brain.

21. The depth probe of claim 18 wherein the balloon is positioned along the distal portion proximal to the element.

* * * * *